(12) United States Patent
Suzuki et al.

(10) Patent No.: US 8,067,527 B2
(45) Date of Patent: Nov. 29, 2011

(54) POLYAMIC ACID AND POLYIMIDE

(75) Inventors: Hideo Suzuki, Funabashi (JP);
Takayuki Tamura, Funabashi (JP);
Yoshikazu Ootsuka, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 377 days.

(21) Appl. No.: 12/373,230

(22) PCT Filed: Jul. 9, 2007

(86) PCT No.: PCT/JP2007/063639
§ 371 (c)(1),
(2), (4) Date: Jan. 9, 2009

(87) PCT Pub. No.: WO2008/007629
PCT Pub. Date: Jan. 17, 2008

(65) Prior Publication Data
US 2009/0292103 A1    Nov. 26, 2009

(30) Foreign Application Priority Data
Jul. 10, 2006  (JP) .................... 2006-189636

(51) Int. Cl.
*C08G 73/00* (2006.01)
(52) U.S. Cl. .............. 528/322; 528/310; 528/335
(58) Field of Classification Search .......... 528/322, 528/310, 335
See application file for complete search history.

(56) References Cited

U.S. PATENT DOCUMENTS

| 3,522,160 A | 7/1970 | Schenck et al. |
| 4,454,310 A | 6/1984 | Oka et al. |
| 2004/0092127 A1 | 5/2004 | Kurosawa et al. |

FOREIGN PATENT DOCUMENTS

| EP | 0 082 724 A1 | 6/1983 |
| EP | 1 418 618 A2 | 5/2004 |
| JP | 58-208322 A | 12/1983 |
| JP | 63-249127 A | 10/1988 |
| JP | 2-24294 B | 5/1990 |
| JP | 2-235842 A | 9/1990 |
| JP | 4-13724 A | 1/1992 |
| JP | 5-341291 A | 12/1993 |
| JP | 2004-149609 A | 5/2004 |
| KR | 2010103034 | * 10/2010 |

OTHER PUBLICATIONS

Klarner et al., Chemische Berichte, 123, pp. 1869-1879, Feb. 19, 1990.

Gauvry et al., Synthesis, No. 4, pp. 574-576, (1999).

* cited by examiner

*Primary Examiner* — James J Seidleck
*Assistant Examiner* — Gregory Listvoyb
(74) *Attorney, Agent, or Firm* — Birch, Stewart, Kolasch & Birch, LLP

(57) ABSTRACT

A polyamic acid comprising at least 10 mol % repeating units represented by the formula [1] or [2]; and a polyimide represented by the formula [3] or [4] which is obtained from the polyamic acid. A polyimide film having high heat resistance and satisfactory in light-transmitting properties and tensile strength is obtained from the polyamic acid.

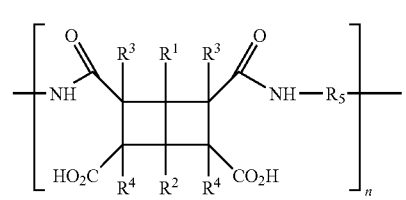

[1]

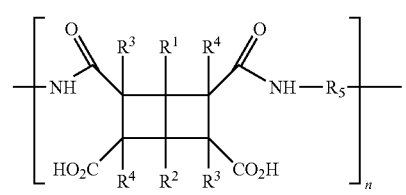

[2]

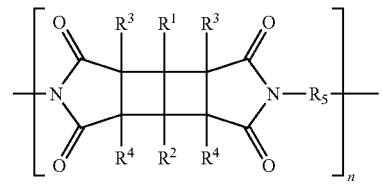

[3]

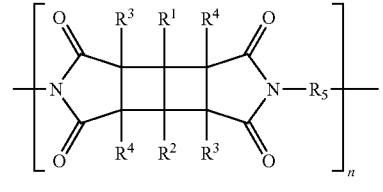

[4]

(In the formulae, $R^1$ and $R^2$ each independently represents hydrogen or $C_{1-10}$ alkyl; $R^3$ and $R^4$ each independently represents hydrogen, halogeno, $C_{1-10}$ alkyl, or phenyl or the $R^3$ and $R^4$ on adjoining carbon atoms are bonded to each other to form $C_{3-8}$ cycloalkyl or phenyl; $R^5$ represents a divalent organic group; and n is an integer of 2 or larger.)

10 Claims, 4 Drawing Sheets

POLYAMIC ACID AND POLYIMIDE

TECHNICAL FIELD

This Invention relates to polyamic acids and polyimides, and more specifically, to polyamic acids and polyimides having alicyclic structures and suitable, for example, as electronic materials.

BACKGROUND ART

Polyimide resins are widely used as electronic materials such as protecting materials and insulating materials in liquid crystal display devices and semiconductors for high mechanical strength, heat resistance, insulating property and solvent resistance as their common characteristic properties. Recently, they are expected to also find utility as optical communication materials such as optical waveguide materials.

In recent years, the developments in these fields are remarkable, resulting in a demand for ever-increasing higher characteristics on materials to be used. Described specifically, such materials are expected to be equipped not only with excellent heat resistance and solvent resistance but also with many performances corresponding to their applications.

As a particularly important property, high transparency can be mentioned. As one of methods for realizing this transparency, it has already been reported to obtain a polyimide, which is relatively low in coloration and has high transparency, by obtaining a polyimide precursor through a polycondensation reaction between an alicyclic tetracarboxylic dianhydride and an aromatic diamine and then imidating the precursor (see Patent Documents 1 and 2).

The development of new polyimides having excellent properties is, however, desired under the situation in recent years that there is also an increasing demand for the use of polyimides of high heat resistance, solvent solubility and transparency in the field of electronic materials making use of light.

As a method for realizing this transparency, a wholly-alicyclic polyimide can be expected by obtaining a wholly-alicyclic polyimide precursor through a polycondensation reaction between an alicyclic tetracarboxylic dianhydride and an alicyclic diamine and then imidating the precursor.

However, a polyimide available from 1,2,3,4-cyclobutane-tetracarboxylic-1,2:3,4-dianhydride (abbreviated as "CBDA"), a representative compound among conventional alicyclic tetracarboxylic dianhydrides, and an alicyclic diamine was so brittle that it was not usable as films. No film made of a wholly-alicyclic polyimide and having stable strength has been found yet accordingly.

There are certain examples in which bicyclo[2.2.0]hexane-2,3,5,6-tetracarboxylic-2,3:5,6-dianhydride (abbreviated as "BHA"), one of monomers for polyamic acids and polyimides of the invention, was synthesized by the following process.

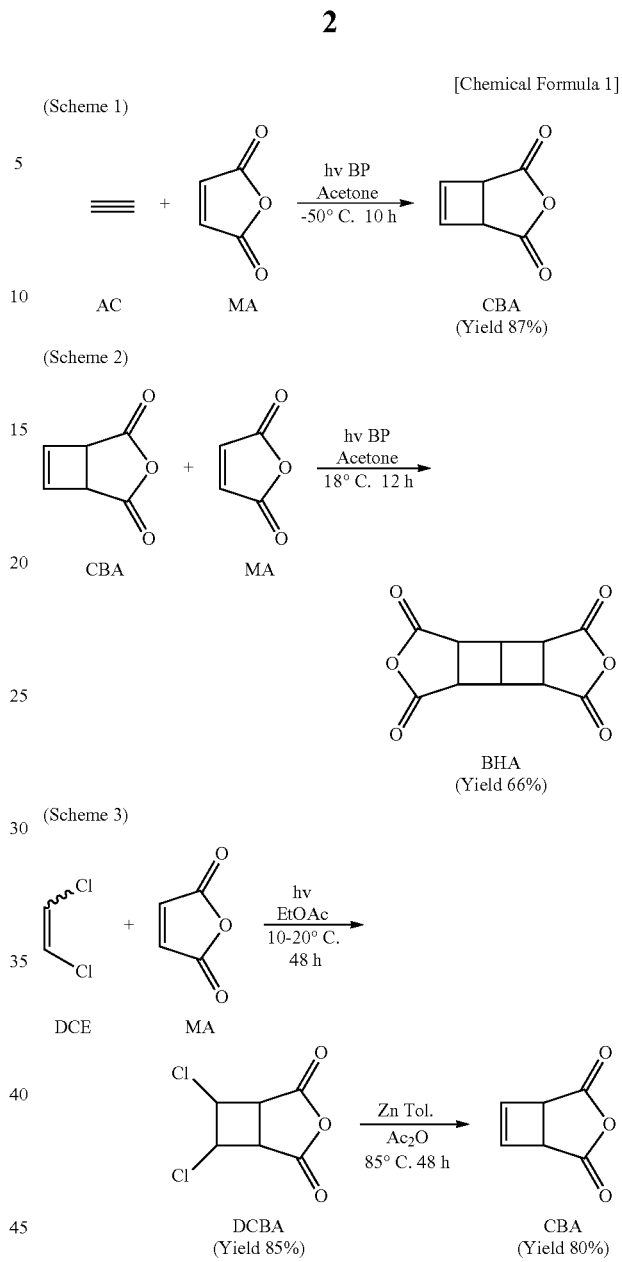

[Chemical Formula 1]

As shown by Scheme 1, 3-cyclobutene-1,2-dicarboxylic anhydride (abbreviated as "CBA") is synthesized by a photoreaction between acetylene (abbreviated as "AC") and maleic anhydride (abbreviated as "MA"). Subsequently, as shown by Scheme 2, BHA is synthesized by a photoreaction between CBA and MA (see Non-patent Document 1).

It is to be noted that as shown by Scheme 3, CBA can also be synthesized by the process that obtains 3,4-dichlorocyclobutane-1,2-dicarboxylic anhydride (abbreviated as "DCBA") through a photoreaction between 1,2-dichloroethylene (abbreviated as "DCE") and MA and then reacts DCBA with zinc and acetic anhydride (see Non-patent Document 2).

There was, however, no example in which a polyamic acid or polyimide was synthesized using BHA.

Patent Document 1: JP-B 2-24294
Patent Document 2: JP-A 58-208322
Non-patent Document 1: Chemische Berichte, 123, 1869-1879 (1990)
Non-patent Document 2: Synthesis, 4, 574-576 (1999)

DISCLOSURE OF THE INVENTION

Problems to be Solved by the Invention

With the foregoing circumstances in view, the present invention has as objects thereof the provision of a polyamic acid, which can afford a polyimide film having high heat resistance and good light transparency and tensile strength, and a polyimide obtainable from the polyamic acid.

Means for Solving the Problem

The present inventors have enthusiastically repeated investigations to achieve the above-described objects. As a result, it has been found that a polyimide film formed using a novel polyimide—which contains the bicyclo[2.2.0]hexane structure as an alicyclic structure, in a predetermined percentage or higher—has heat resistance as high as 300° C. or higher in terms of heat decomposition temperature and also good transparency and tensile strength, and therefore, can be used as an electronic material such as a protecting material or insulating material in liquid crystal display devices and semiconductors and also as an optical communication material such as optical waveguides.

Described specifically, the present invention provides:

1. A polyamic acid including at least 10 mol % of repeating units represented by the formula [1] or formula [2],

[Chemical Formula 2]

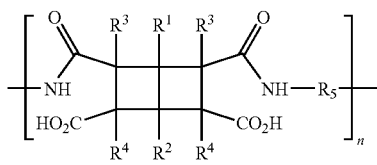

[1]

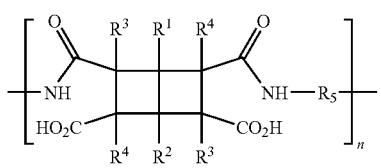

[2]

wherein $R^1$ and $R^2$ each independently represent a hydrogen atom or an alkyl group having 1 to 10 carbon atoms, $R^3$ and $R^4$ each independently represent a hydrogen atom, a halogen atom, an alkyl group having 1 to 10 carbon atoms, a phenyl group, or $R^3$ and $R^4$ on adjacent carbon atoms are fused together to represent a cycloalkyl group having 3 to 8 carbon atoms or to represent a phenyl group, $R^5$ represents a divalent organic group, and n stands for an integer of at least 2;

2. A polyimide including at least 10 mol % of repeating units represented by the formula [3] or formula [4],

[Chemical Formula 3]

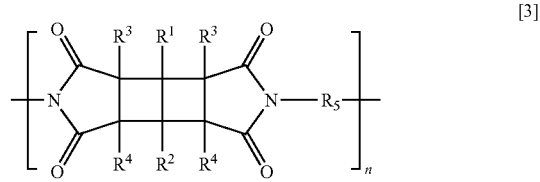

[3]

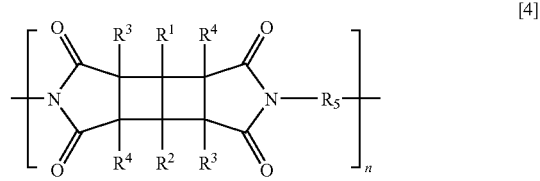

[4]

wherein $R^1$ and $R^2$ each independently represent a hydrogen atom or an alkyl group having 1 to 10 carbon atoms, $R^3$ and $R^4$ each independently represent a hydrogen atom, a halogen atom, an alkyl group having 1 to 10 carbon atoms, a phenyl group, or $R^3$ and $R^4$ on adjacent carbon atoms are fused together to represent a cycloalkyl group having 3 to 8 carbon atoms or to represent a phenyl group, $R^5$ represents a divalent organic group, and n stands for an integer of at least 2;

3. A polyamic acid as described above under 1., which has a number average molecular weight of 5,000 to 300,000;

4. A polyamic acid as described above under 1., wherein $R^1$, $R^2$, $R^3$ and $R^4$ are a hydrogen atom;

5. A polyamic acid as described above under 1., wherein $R^1$ and $R^2$ are a hydrogen atom, and at least one of $R^3$ and $R^4$ is a methyl group;

6. A polyimide as described above under 2., wherein $R^1$, $R^2$, $R^3$ and $R^4$ are a hydrogen atom;

7. A polyimide as described above under 2., wherein $R^1$ and $R^2$ are a hydrogen atom, and at least one of $R^3$ and $R^4$ is a methyl group;

8. A polyamic acid as described above under 1., wherein in the formula [1] and formula [2], $R^5$ is a divalent organic group derived from an alicyclic diamine or aliphatic diamine;

9. A polyimide as described above under 2., wherein in the formula [3] and formula [4], $R^5$ is a divalent organic group derived from an alicyclic diamine or aliphatic diamine;

10. A tetracarboxylic dianhydride represented by the formula [5],

[Chemical Formula 4]

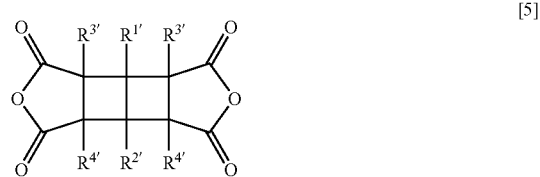

[5]

wherein $R^{1'}$ and $R^{2'}$ each independently represent a hydrogen atom or an alkyl group having 1 to 10 carbon atoms, and $R^{3'}$ and $R^{4'}$ each independently represent a hydrogen atom, a halogen atom, an alkyl group having 1 to 10 carbon atoms, a phenyl group, or $R^{3'}$ and $R^{4'}$ on adjacent carbon atoms are fused together to represent a cycloalkyl group having 3 to 8 carbon atoms or to represent a phenyl group, with a proviso that $R^{1\prime}$, $R^{2\prime}$, $R^{3\prime}$ and $R^{4\prime}$ do not represent hydrogen atoms, respectively, at the same time;
11. A tetracarboxylic dianhydride represented by the formula [6],

[Chemical Formula 5]

$$[6]$$

$$\begin{array}{c} O \quad R^{3\prime} \ R^{1\prime} \ R^{4\prime} \quad O \\ \text{(structure)} \\ O \quad R^{4\prime} \ R^{2\prime} \ R^{3\prime} \quad O \end{array}$$

wherein $R^{1\prime}$ and $R^{2\prime}$ each independently represent a hydrogen atom or an alkyl group having 1 to 10 carbon atoms, and $R^{3\prime}$ and $R^{4\prime}$ each independently represent a hydrogen atom, a halogen atom, an alkyl group having 1 to 10 carbon atoms, a phenyl group, or $R^{3\prime}$ and $R^{4\prime}$ on adjacent carbon atoms are fused together to represent a cycloalkyl group having 3 to 8 carbon atoms or to represent a phenyl group, with a proviso that $R^{1\prime}$, $R^{2\prime}$, $R^{3\prime}$ and $R^{4\prime}$ do not represent hydrogen atoms, respectively, at the same time; and
12. A film including a polyimide as described above under any one of 2., 6., 7. and 9.

Effects of the Invention

The polyamic acid and polyimide of the invention afford polyimide films having high heat resistance and good light transparency and tensile strength. The polyimide of the invention, which has such properties, is expected to find utility as an electronic material such as a protecting material or insulating material in liquid crystal display devices and semiconductors and also as an optical communication material such as optical waveguides.

BEST MODE FOR CARRYING OUT THE INVENTION

Figure 1:
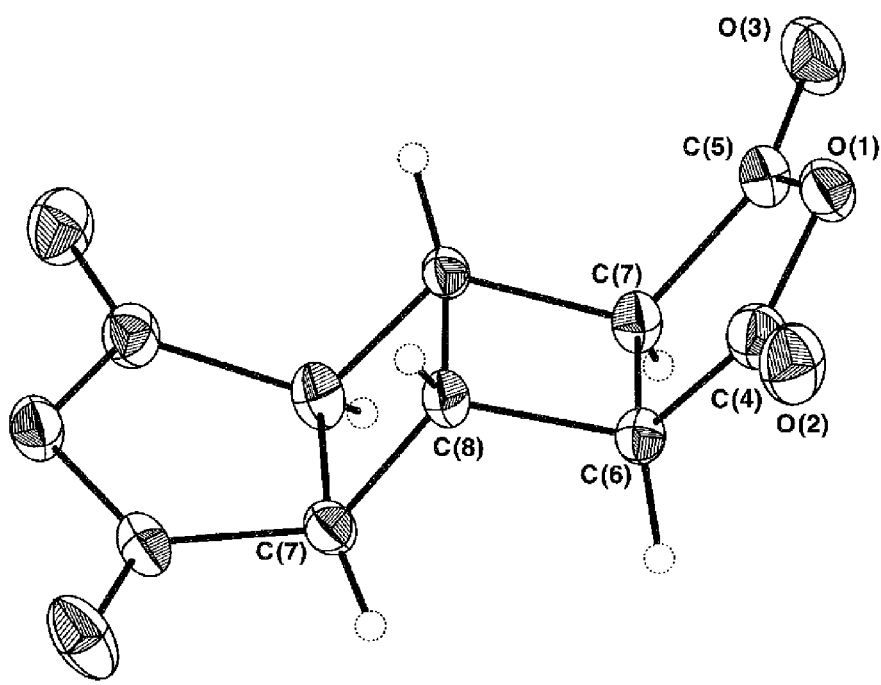
FIG. 1 is an X-ray ORTEP diagram of BHA.

The present invention will hereinafter be described in further detail.
The polyamic acid of the invention contains at least 10 mol % of repeating units represented by the formula [1] or [2]. On the other hand, the polyimide of the invention is a polyimide derived from the polyamic acid, and contains at least 10 mol % of repeating units represented by the formula [3] or [4].

[Chemical Formula 6]

$$[1]$$

$$[2]$$

$$[3]$$

$$[4]$$

In the above-described individual formulas, $R^1$ and $R^2$ each independently represent a hydrogen atom or an alkyl group having 1 to 10 carbon atoms; $R^3$ and $R^4$ each independently represent a hydrogen atom, a halogen atom, an alkyl group having 1 to 10 carbon atoms, a phenyl group, or $R^3$ and $R^4$ on adjacent carbon atoms are fused together to represent a cycloalkyl group having 3 to 8 carbon atoms or to represent a phenyl group; $R^5$ represents a divalent organic group; and n stands for an integer.

Specific examples of the alkyl group having 1 to 10 carbon atoms include methyl, ethyl, n-propyl, i-propyl, n-butyl, i-butyl, s-butyl, n-amyl, i-amyl, s-amyl, n-hexyl, n-heptyl, n-octyl, n-nonyl, n-decyl, and the like.

As the cycloalkyl group having 3 to 8 carbon atoms, cyclopropyl, cyclobutyl, cyclopentyl, cyclohexyl, cycloheptyl, cyclooctyl or the like can be mentioned.

As the halogen atom, F, Cl, Br or I can be mentioned.

Especially in view of the availability of starting materials, production yield and the like, $R^1$ and $R^2$ may each preferably be a hydrogen atom, $R^3$ and $R^4$ may each preferably be a hydrogen atom or a methyl group. Among such compounds, suited are compounds in which all of $R^1$ to $R^4$ are hydrogen atoms; and compounds in which $R^1$ and $R^2$ are hydrogen atoms, respectively, and at least one of $R^3$ and $R^4$ is a methyl group.

$R^5$ is a divalent organic group, and is an organic group derived from the organic diamine reacted with the tetracarboxylic dianhydride (BHA compound).

As the diamine that gives this divalent organic group, various diamines conventionally employed in the synthesis of polyimides are usable. Illustrative are aromatic diamines such as p-phenylenediamine (p-PDA), m-phenylenediamine, 2,5-diaminotoluene, 2,6-diaminotoluene, 1,3-bis(4,4'-aminophenoxy)benzene (DA-4P), 4,4'-diamino-1,5-phenoxypentane (PA-5MG), 4,4'-diaminobiphenyl, 3,3'-dimethyl-4,4'-diaminobiphenyl, 3,3'-dimethoxy-4,4'-diaminobiphenyl, 4,4'-diaminodiphenyl ether (DDE), 4,4'-diaminodiphenylmethane (DDM), 2,2'-diaminodiphenylpropane, bis(3,5-diethyl-4-aminophenyl)methane, diaminodiphenylsulfone, diaminobenzophenone, diaminonaphthalene, 1,4-bis(4-aminophenoxy)benzene, 1,4-bis(4-aminophenyl)benzene, 9,10-bis(4-aminophenyl)anthracene, 1,3-bis(4-aminophenoxy)benzene, 4,4'-bis(4-aminophenoxy)diphenylsulfone, 2,2-bis[4-(4-aminophenoxy)phenyl]propane, 2,2'-trifluoromethyl-4,40-diaminobiphenyl, and neopentyl glycol bis(4-aminophenyl) ether;

alicyclic diamines such as 1,4-diaminocyclohexane, 1,4-cyclohexanebis(methylamine), 4,4'-diaminodicyclohexylmethane, bis(4-amino-3-methylcyclohexyl)methane, 3(4), 8(9)-bis(aminomethyl)tricyclo[5.2.1.0$^{2,6}$]decane, 2,5(6)-bis(aminomethyl)bicyclo[2.2.1]heptane (BBH), 1,3-diaminoadamantane, 3,3'-diamino-1,1'-biadamantyl, and 1,6-diaminodiadamantane(1,6-aminopentanecyclo-[7.3.1.1$^{4,12}$,0$^{2,7}$,0$^{6,11}$]tetradecane;

aliphatic diamines such as tetramethylenediamine and hexamethylenediamine; and the like.

These diamines can be used either singly or in combination of two or more thereof upon synthesis of the polyamic acid (polyimide). When two or more of them are used in combination, $R^5$ becomes a combination of two or more divalent organic groups.

Among these diamines, the alicyclic diamines or aliphatic diamines may each be used preferably because the resulting polyamic acid of the present invention and the polyimide obtained from the polyamic acid are provided with still higher transparency.

Subscript n can be any integer of 2 or greater. When the below-described molecular weight of the polyamic acid is taken into consideration, however, an integer of 10 to 2,000 is preferred, with an integer of 20 to 1,000 being more preferred.

The molecular weight of the polyamic acid may be preferably 3,000 to 500,000, more preferably 5,000 to 300,000 in terms of number average molecular weight when the strength after formation into a polyimide film and the processability upon formation into a film are taken into consideration.

It is to be noted that the number average molecular weights are measurement values by gel permeation chromatography (hereinafter called "GPC").

For similar reasons as described above, the polymerization degree of the polyimide may preferably be 0.05 to 5.0 dL/g in terms of the reduced viscosity of a polyamic acid solution (in N-methylpyrrolidone of 30° C.; concentration: 0.5 g/dL).

The polyamic acid (polyimide) of the invention is required to contain at least 10 mol % of the repeating structure represented by the formula [1] or formula [2] (or the formula [3] or [4]). Especially to provide the polyimide with high heat resistance and transparency and excellent solvent solubility, the polyamic acid (polyimide) of the invention may contain preferably 50 mol % or more, more preferably 70 mol % or more, optimally 90 mol % or more of the above-described structure.

The polyimide of the invention can be obtained by way of thermal imidation of the inventive polyamic acid obtained by reacting the BHA compound and optionally any other tetracarboxylic acid derivative with the above-mentioned various diamines in a solvent. As an alternative, the polyamic acid can be converted into an imide in a solvent and the imide can be used as a solvent-soluble polyimide.

No particular limitation is imposed on the production process of the polyamic acid. For example, it can be obtained by subjecting the BHA compound and optionally any other tetracarboxylic acid derivative with the diamine to solution polymerization.

It is to be noted that in the present invention, the BHA compound is used for at least 10 mol % of the whole mole number of the tetracarboxylic acid derivative.

A description will first be made about a process for the production of the BHA compound. The BHA compound can be produced in accordance with the following scheme.

[Chemical Formula 7]

wherein $R^1$ to $R^4$ have the same meanings as defined above.

Namely, the process is a one that subjects the acetylene derivative and the maleic anhydride derivative to a photoreaction. The photoreaction may be conducted preferably in the presence of a photosensitizer such as benzophenone, acetophenone or the like. As a light source, it is preferred to use a high-pressure mercury vapor lamp.

As a reaction solvent, a lower ketone compound such as acetone or methyl ethyl ketone is preferred.

As the reaction temperature for the former step that obtains a cyclobutenedicarboxylic anhydride intermediate, a low temperature of −80 to −20° C. is preferred. As the reaction temperature for the latter step that obtains BHA from the cyclobutenedicarboxylic anhydride intermediate, 0 to 50° C. is preferred.

As the acetylene derivative and maleic anhydride derivative, most economical materials are acetylene and maleic anhydride in which all of $R^1$ to $R^4$ are hydrogen atoms.

As another process, a route shown by the following scheme can be contemplated.

[Chemical Formula 8]

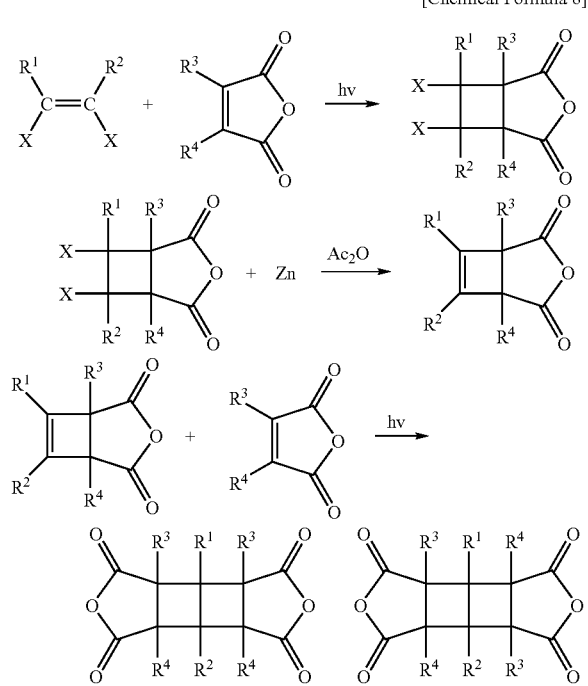

wherein R¹ to R⁴ have the same meanings as defined above, and X represents a halogen atom.

This process has an advantage in that it does not require such a low temperature as required in the photoreaction in the former step of the above-mentioned production process.

As the 1,2-dihalogenoethylene derivative and maleic anhydride derivative, most economical materials are 1,2-dichloroethylene and maleic anhydride in which all of R¹ to R⁴ are hydrogen atoms.

By a photoreaction at 10 to 20° C. between 1,2-dichloroethylene and maleic anhydride, 3,4-dichlorocyclobutane-1,2-dicarboxylic anhydride (DCBA) intermediate is synthesized. Using it together with zinc and acetic anhydride, cyclobut-3-ene-1,2-dicarboxylic anhydride (CBA) intermediate is then synthesized. The step that obtains BHA from CBA is the same as mentioned above.

As will be mentioned subsequently herein, it has been confirmed by an X-ray structure analysis that each of the principal components of BHA obtained by this production process is in the exo-exo form (see FIG. 1).

Either singly or in combination, they can be similarly used as a monomer for a polycondensation reaction with the diamine compounds.

The polyamic acid of the invention produced using such an acid dianhydride and represented by the planar structural formula [1] or [2] and the polyimide of the present invention produced using such an acid dianhydride and represented by the planar structural formula [3] or [4] include stereoisomers corresponding to the respective acid dianhydrides.

Specific examples of the other tetracarboxylic acid derivative which may be used optionally include alicyclic tetracarboxylic acids such as 1,2,3,4-tetracarboxylic acid, 2,3,4,5-tetrahydrofurantetracarboxylic acid, 1,2,4,5-cyclohexanoic acid, 3,4-dicarboxy-1-cyclohexylsuccinic acid, 3,4-dicarboxy-1,2,3,4-tetrahydro-1-napthalenesuccinic acid and bicyclo[3.3.0]octane-2,4,6,8-tetracarboxylic acid, and their dianhydrides and their dicarboxylic acid diacid dihalides; aromatic tetracarboxylic acids such as pyromellitic acid, 2,3,6,7-naphthalenetetracarboxylic acid, 1,2,5,6-naphthalenetetracarboxylic acid, 1,4,5,8-naphthalenetetracarboxylic acid, 2,3,6,7-anthracenetetracarboxylic acid, 1,2,5,6-anthracenetetracarboxylic acid, 3,3',4,4'-biphenyltetracarboxylic acid, 2,3,3',4-biphenyltetracarboxylic acid, bis(3,4-dicarboxyphenyl)ether, 3,3',4,4'-benzophenonetetracarboxylic acid, bis(3,4-dicarboxyphenyl)methane, 2,2-bis(3,4-dicarboxyphenyl)propane, 1,1,1,3,3,3-hexafluoro-2,2-bis(3,4-dicarboxyphenyl)propane, bis(3,4-dicarboxyphenyl)dimethylsilane, bis(3,4-dicarboxyphenyl)diphenylsilane, 2,3,4,5-pyridinetetracarboxylic acid and 2,6-bis(3,4-dicarboxyphenyl)pyridine, and their dianhydrides and their dicarboxylic acid diacid dihalides; and the like.

The molar ratio of the diamine to the BHA compound and other tetracarboxylic dianhydride upon production of the polyamic acid may preferably be 0.8 to 1.2. Similar to general polycondensation reactions, the resulting polymer is provided with a greater polymerization degree as the molar ratio becomes closer to 1. An excessively small polymerization degree may lead to a polyimide film of insufficient strength, while an unduly large polymerization degree may result in reduced workability upon formation of a polyimide film.

As the temperature of the solution polymerization, a desired temperature of from −20 to 150° C. can be adopted, with −5 to 100° C. being preferred.

Specific examples of the solvent usable for the solution polymerization include m-cresol, N-methyl-2-pyrrolidone, N,N-dimethylformamide, N,N-dimethylacetamide, N-methylcaprolactam, dimethyl sulfoxide, tetramethylurea, pyridine, dimethyl sulfone, hexamethylphosphoramide (HMPA), γ-butyrolactone, and the like. These solvents may be used either singly or in combination or two or more thereof. Further, the above-described solvent may also be used after adding one or more solvents, which do not dissolve the polyamic acid, to an extent that a homogeneous solution is obtainable.

No particular limitation is imposed on the method for converting the polyamic acid into the polyamide, but generally adopted is the method that subjects the polyamic acid, which has been obtained as described above, to cyclodehydration with heating. It is also possible to adopt the method that uses a conventionally-known cyclodehydration catalyst to achieve chemical ring closure.

As the temperature upon conducting ring closure with heating, it is possible to choose a desired temperature of from 100 to 300° C., with 120 to 250° C. being preferred.

When achieving chemical ring closure, usable examples of the cyclodehydration catalyst include pyridine, triethylamine, acetic anhydride and the like. Upon conducting the chemical ring closure, a desired temperature of from −20 to 200° C. can be chosen as the reaction temperature.

The polyimide solution obtained as described above may be used as it is. It is also possible to have the polyimide precipitated and isolated by adding a poor solvent such as methanol or ethanol and to use the polyimide as a powder; or to redissolve the polyimide powder in a suitable solvent to use the polyimide as a solution.

No particular limitation is imposed on the solvent for use in the redissolution insofar as it can dissolve the resultant polyimide. Illustrative are m-cresol, 2-pyrrolidone, N-methylpyrrolidone, N-ethylpyrrolidone, N-vinylpyrrolidone, N,N-dimethylacetamide, N,N-dimethylformamide, hexamethylphosphoramide (HMPA), and γ-butyrolactone.

Further, even if a solvent cannot dissolve the polyimide by itself, the solvent can still be used by adding it to above-described solvent to an extent that the solubility is not impaired. Specific examples of such a solvent include ethylcellosolve, butylcellosolve, ethyl carbitol, butyl carbitol, ethyl carbitol acetate, ethylene glycol, 1-methoxy-2-propanol, 1-ethoxy-2-propanol, 1-butoxy-2-propanol, 1-phenoxy-2-propanol, propylene glycol monoacetate, propylene glycol diacetate, propylene glycol-1-monomethyl ether-2-acetate, propylene glycol-1-monoethyl ether-2-acetate, dipropylene glycol, 2-(2-ethoxypropoxy)propanol, methyl lactate ester, ethyl lactate ester, n-propyl lactate ester, n-butyl lactate ester, isoamyl lactate ester, and the like.

To further improve the adhesion between a polyimide film and a substrate, an additive such as a coupling agent may be added to the resultant polyimide solution.

A polyimide film can be formed on a substrate by coating the polyimide solution of the invention on the substrate and causing the solvent to evaporate. During the evaporation of the solvent, the temperature may generally be 100 to 300° C. or so.

Moreover, the present invention also provides a tetracarboxylic dianhydride represented by the formula [5] and formula [6].

[Chemical Formula 9]

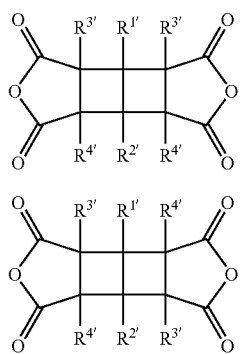

wherein $R^{1\prime}$ and $R^{2\prime}$ each independently represent a hydrogen atom or an alkyl group having 1 to 10 carbon atoms; and $R^{3\prime}$ and $R^{4\prime}$ each independently represent a hydrogen atom, a halogen atom, an alkyl group having 1 to 10 carbon atoms, a phenyl group, or $R^{3\prime}$ and $R^{4\prime}$ on adjacent carbon atoms are fused together to represent a cycloalkyl group having 3 to 8 carbon atoms or to represent a phenyl group; with a proviso that $R^{1\prime}$, $R^{2\prime}$, $R^{3\prime}$ and $R^{4\prime}$ do not represent hydrogen atoms, respectively, at the same time.

Specific examples of the alkyl group having 1 to 10 carbon atoms include methyl, ethyl, n-propyl, i-propyl, n-butyl, i-butyl, s-butyl, n-amyl, i-amyl, s-amyl, n-hexyl, n-heptyl, n-octyl, n-nonyl, n-decyl, and the like.

As the cycloalkyl group having 3 to 8 carbon atoms, cyclopropyl, cyclobutyl, cyclopentyl, cyclohexyl, cycloheptyl, cyclooctyl or the like can be mentioned.

As the halogen atom, F, Cl, Br or I can be mentioned.

Especially in view of the availability of starting materials, production yield and the like, preferred are compounds in which $R^{1\prime}$ and $R^{2\prime}$ each represent a hydrogen atom and at least one of $R^{3\prime}$ and $R^{4\prime}$ is a methyl group.

EXAMPLES

The present invention will hereinafter be described more specifically based on Synthesis Examples and Examples. It should, however, be borne in mind that the present invention shall not be limited to the following Examples. The followings are measuring instruments and conditions for respective physical properties.

[1] Molecular Weight
  Instrument: Room-temperature GPC measuring instrument ("SSC-7200" manufactured by Senshu Scientific Co., Ltd.)
  Eluent: DMF
[2] TG/DTA (Thermogravimety/Differential Thermal Analyzer)
  Instrument: "THERMOPLUS TG8120" (manufactured by Rigaku Corporation)
[3] NMR
  Instrument: FT-NMR system "MODEL JNM-LA400" (manufactured by JOEL Ltd.)
  Measuring solvent: DMSO-$d_6$
[4] Single-Crystal X-Ray
  Instrument; "DIP2030" (manufactured by Mac Science Company Ltd.)
  X-ray: MoKα (40 kV, 200 mA)
  Temperature: Room temperature
[5] FT-IR
  Instrument: "NICOLET 5700" (Thermo Electron Corporation)
[6] Thickness
  Instrument: "SURFCORDER ET 4000A" (fully-automated microprofile measuring instrument) (Kosaka Laboratory Ltd.)
[7] UV-Vis Spectrum
  Instrument: "UV-VIS-NIR SCANNING SPECTROPHOTOMETER" (recording spectrophotometer) (manufactured by Shimadzu Corporation)
[8] Conditions for Tensile Test
  1) Load detector: 5 kg max load cell
  2) Elongation detector: Linear cage 5 mm max
  3) Chucks; WC stress relief grips
  4) Rate of pulling: 0.4 mm/min Synthesis Example 1

Synthesis of BHA

[Chemical Formula 10]

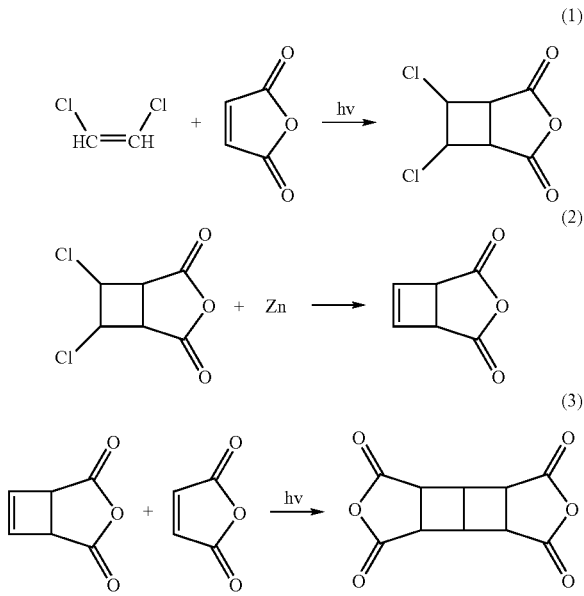

(1) Synthesis of Intermediate DCBA

After cis-1,2-dichloroethylene (65.2 g, 673 mmol), maleic anhydride (60 g, 612 mmol) and ethyl acetate (1,200 g) were charged into a 2,000 mL photoreactor made of "PYLEX"® glass and were stirred at room temperature into a solution, the solution was irradiated at 21 to 23° C. for 48 hours under stirring by a 400 W high-pressure mercury lamp (internal irradiation).

After the reaction, the reaction mixture was concentrated to obtain crystals (105.6 g). Toluene (180 g) was added dropwise to the crystals, and the resulting mixture was heated under reflux into a slurry. At 80° C., hexane (180 g) was then added dropwise, followed by stirring. The resulting solution was allowed to cool down to 20° C. while being left at rest. Precipitated crystals were collected by filtration, washed with toluene and with hexane, each once, and then dried to afford white crystals (94.6 g, yield: 79.3%).

From a $^1$H-NMR spectrum, those crystals were confirmed to be 3,4-dichlorocyclobutane-1,2-dicarboxylic anhydride (abbreviated as "DCBA").

(2) Synthesis of Intermediate CBA

DCBA (50 g, 256.4 mmol) and toluene (500 g) were charged into a 1,000 mL reactor made of "PYLEX"® glass, and under stirring at room temperature, acetic anhydride (131 g) was added dropwise. After the resultant mixture was heated to 40° C., zinc powder (168 g) was added. The mixture was then heated to 85° C., at which the mixture was stirred for 30 hours. The thus-obtained mixture was allowed to cool down and was then filtered through Celite by decantation. The filtrate was concentrated to obtain crystals (40.0 g). Those crystals were washed with toluene and with hexane, each once, and then dried to obtain brown crystals (16 g). Using a Kugelrohr distillation oven, distillation was then conducted at an external temperature of 135° C. under reduced pressure to afford pale yellow crystals (11.0 g, yield: 34.6%).

From a $^1$H-NMR spectrum, those crystals were confirmed to be cyclobut-3-ene-1,2-dicarboxylic anhydride (abbreviated as "CBA").

(3) Synthesis of BHA

After the intermediate CBA (11 g, 88.65 mmol), maleic anhydride (8.69 g, 88.65 mmol) and benzophenone (7.35 g, 39.89 mmol) and acetone (160 g) were charged into a 300 mL photoreactor made of "PYLEXT"® glass and were stirred at room temperature into a solution, the solution was irradiated at 15 to 20° C. for 61 hours under stirring by a 100 W high-pressure mercury lamp (internal irradiation), resulting in the precipitation of crystals. After the reaction, the reaction mixture was concentrated to 143 g. Subsequent to filtration, the crystals were repeatedly washed with acetone (once) and with hexane (thrice), and then dried to afford white crystals (5.0 g, yield: 25.4%). The filtrate was left at rest to afford secondary crystals (0.76 g, yield: 3.9%).

From the following analysis results, those crystals were confirmed to be BHA.

$^1$H-NMR (DMSO-d$_6$; δ ppm): 3.17 (s, 2H), 3.95 (s, 4H)

$^{13}$C-NMR (DMSO-d$_6$; δ ppm): 40.55 (2), 45.34 (4), 172.5 (4)

TG-DTA: Decomposition temperature: 324.4° C.

Those crystals were dissolved in acetonitrile (with acetic anhydride added therein), and the resulting solution was allowed to naturally concentrate such that single crystals were formed. From an X-ray structural analysis, their stereostructure was ascertained (see Table 1 and FIG. 1).

TABLE 1

Crystallographic parameters of BHA

| Molecule | $C_{10}H_6O_4$ |
|---|---|
| Crystal system | Tetragonal |
| Space group | $P4_12_12$ |
| Lattice constants | a(Å) = 6.689(1) |
| | c(Å) = 19.902(1) |
| | v(Å$^3$) = 890.5(1) |
| Z | 4 |
| R | 0.08 |

Example 1

Synthesis of BHA-p-PDA Polyamic Acid and Polyimide

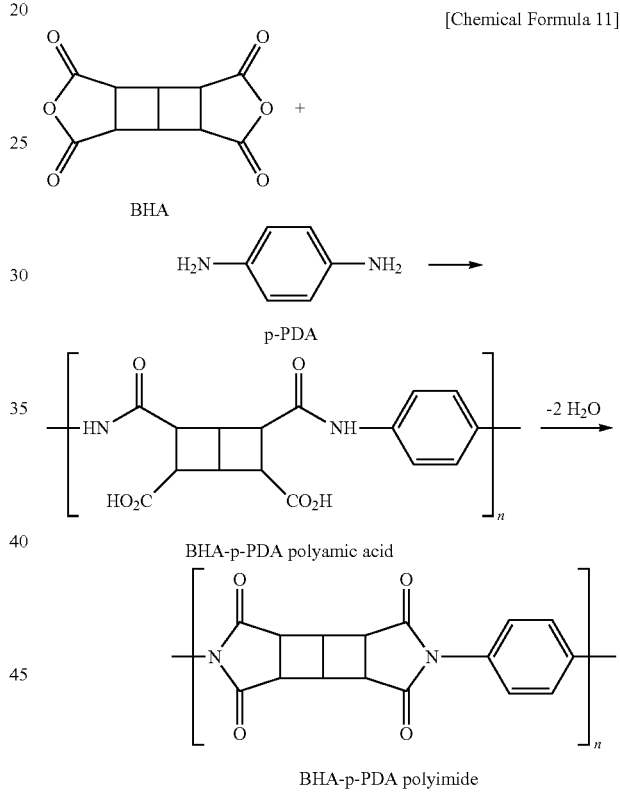

[Chemical Formula 11]

BHA-p-PDA polyamic acid

BHA-p-PDA polyimide p-Phenylenediamine (p-PDA) (0.324 g, 3.00 mmol) and 1-methyl-2-pyrrolidone (NMP) (8.9 g, solid content; 10 wt %) were charged into a dried 4-necked reaction flask, and were then formed at 18° C. (room temperature) into a solution while stirring them with a mechanical stirrer. Subsequently, BHA (0.666 g, 3.00 mmol) was added, followed by stirring at 20° C. and 160 rpm for 24 hours with the mechanical stirrer.

At that time point, the resultant BHA-p-PDA polyamic acid polymerization solution was sampled and measured for its molecular weight. As a result of a measurement by GPC, its number average molecular weight (Mn) was 16,717, its weight average molecular weight (Mw) was 17,191, and Mw/Mn was 1.028.

<Formation of Polyimide Film>

The thus-obtained BHA-p-PDA polyamic acid polymerization solution was coated onto 8 cm×10 cm glass plates by using (1) a 25 μm doctor blade and (2) a 200 μm doctor blade, respectively. Subsequently, the coatings were prebaked at 100° C. for 30 minutes by using a hot plate, and the glass plates with the prebaked coatings carried thereon were then transferred into a drier, in which baking was conducted at 230° C. for 1 hour to form polyimide films.

<Measurement of Polyimide Film Thickness>

Using a fully-automated microfigure measuring instrument, the thicknesses of the films were measured. As a result, the film obtained by coating the polymerization solution at 25 μm (1) was 0.96 μm thick, and the film obtained by coating the polymerization solution at 200 μm (1) was 9.36 μm thick.

<Measurement of Imidation Rate>

The polyimide films were measured by FT-IR, and from their absorption spectra, their imidation rates were calculated to be 100% in the 0.96 μm thick film (1) and 100% in the 9.36 μm thick film (2) (each calculated from the absorption by the remaining amide: the area at 1630 to 1650 $cm^{-1}$ and the absorption of the formed imide: the area at 1774 to 1698 $cm^{-1}$).

<Measurement of Light Transmittance>

Figure 2:
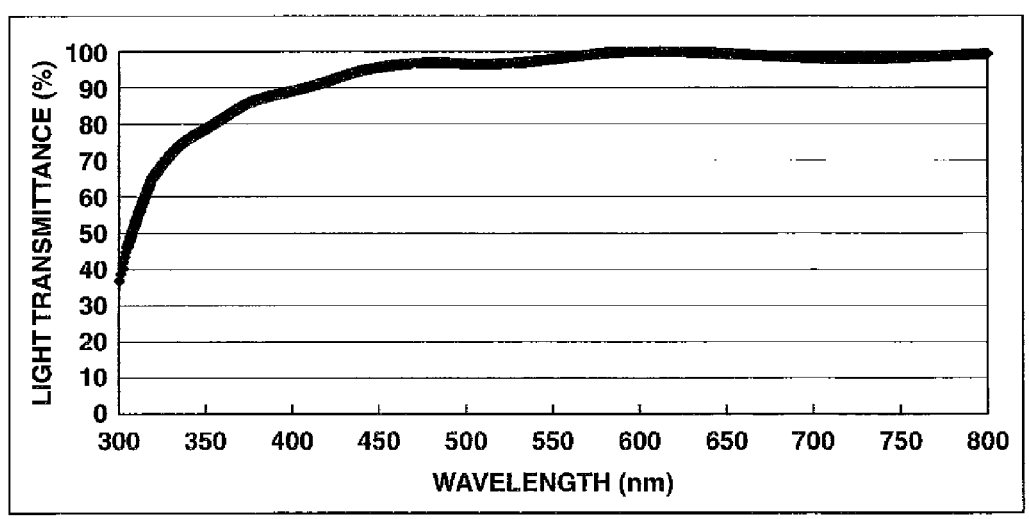
FIG. 2 is a UV-Vis spectrum of a BHA-p-PDA polyimide of 0.96 μm in film thickness.

As a result of measurements of UV-Vis spectra, the 0.96 μm thick film (1) had a light transmittance of 80% at 350 nm, and a light transmittance of 90% at 400 nm (see FIG. 2).

Further, thermal characteristics of the 9.36 μm thick film (2) were as follows:

5% weight loss temperature ($T_5$): 269.2° C.

10% weight loss temperature ($T_{10}$): 321.1° C.

Example 2

Synthesis of BHA-DDE Polyamic Acid and Polyimide

[Chemical Formula 12]

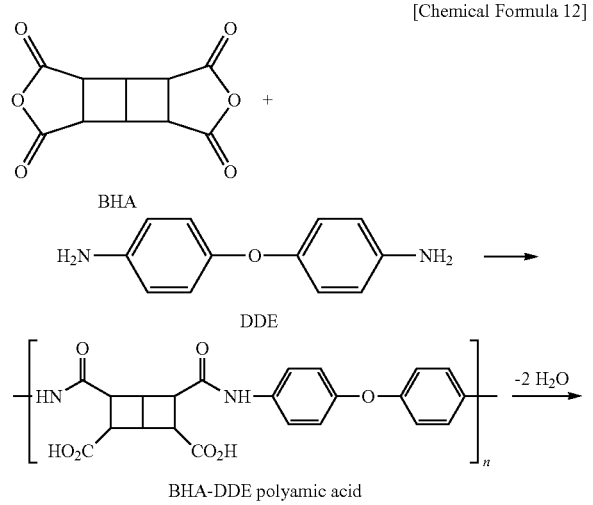

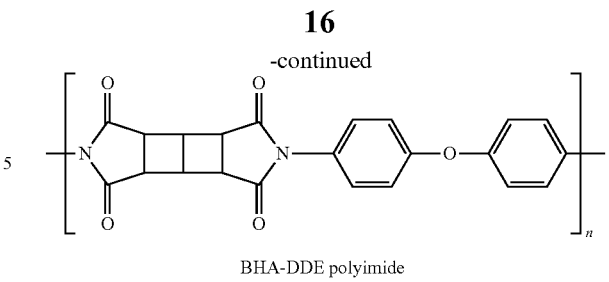

BHA-DDE polyimide 4,4'-Diaminodiphenyl ether (DDE) (0.601 g, 3.00 mmol) and NMP (11.4 g, solid content: 10 wt %) were charged into a dried 4-necked reaction flask, and were then formed into a solution at 18° C. (room temperature) while stirring them with a mechanical stirrer. Subsequently, BHA (0.666 g, 3.00 mmol) was added, followed by stirring at 18° C. and 160 rpm for 24 hours with the mechanical stirrer.

At that time point, the resultant BHA-DDE polyamic acid polymerization solution was sampled and measured for its molecular weight. As a result of a measurement by GPC, its number average molecular weight (Mn) was 23,593, its weight average molecular weight (Mw) was 24,215, and Mw/Mn was 1.026.

In a similar manner as in Example 1, polyimide films were next formed, and their thicknesses, imidation rates and light transmittances were measured. The results are shown in the following table.

TABLE 2

| Polyimide film | Doctor blade (μm) | Film thickness (μm) | Imidation rate (%) | Light transmittance (%) | |
| --- | --- | --- | --- | --- | --- |
| | | | | 350 (nm) | 400 (nm) |
| 1 | 25 | 0.68 | 99 | 80 | 89 |
| 2 | 200 | 8.50 | 100 | — | 35 |

<Measurement of Light Transmittance>

Figure 3:
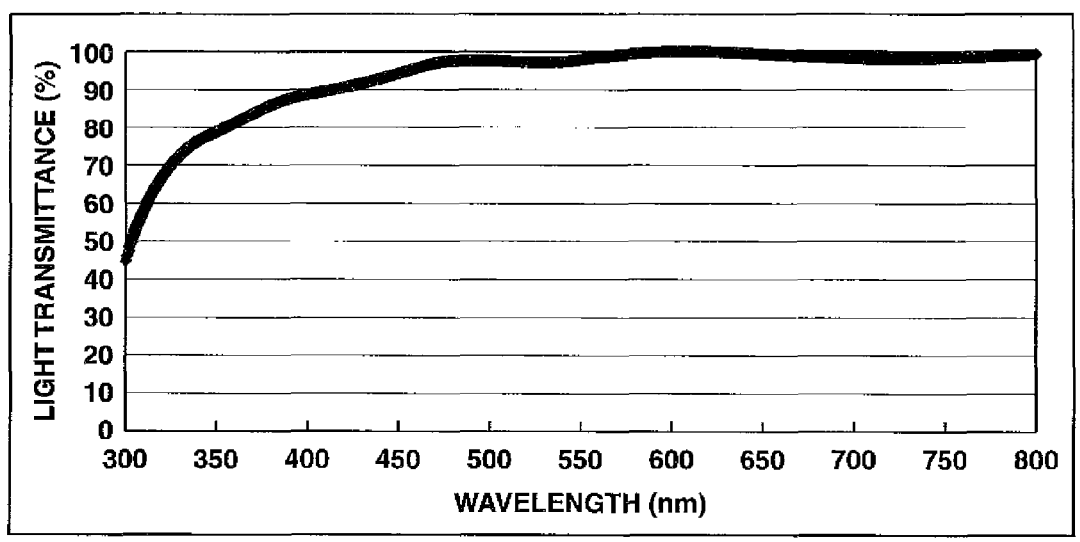
FIG. 3 is a UV-Vis spectrum of a BHA-DDE polyimide of 0.68 μm in film thickness.

As a result of measurements of UV-Vis spectra, the polyimide film 1 had a light transmittance of 80% at 350 nm, and a light transmittance of 89% at 400 nm (see FIG. 3).

Further, thermal characteristics of the polyimide film 2 were as follows:

5% weight loss temperature ($T_5$): 297.9° C.

10% weight loss temperature ($T_{10}$): 352.8° C.

Example 3

Synthesis of BHA-PA-5MG Polyamic Acid and Polyimide

[Chemical Formula 13]

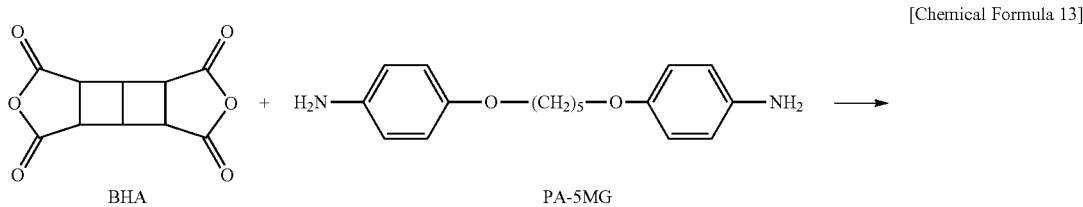

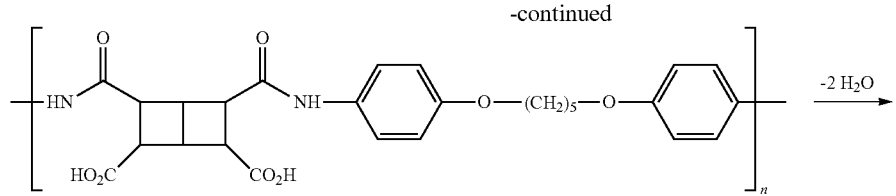

BHA-PA-5MG polyamic acid

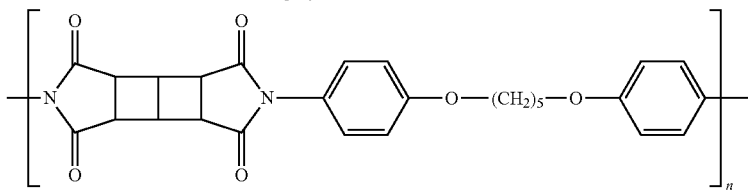

BHA-PA-5MG polyimide 4,4'-Diamino-1,5-phenoxypentane (PA-5MG) (0.573 g, 2.00 mmol) and NMP (10.0 g, solid content: 10 wt %) were charged into a dried 4-necked reaction flask, and were then formed into a solution at 18° C. (room temperature) while stirring them with a mechanical stirrer. Subsequently, BHA (0.444 g, 2.00 mmol) was added, followed by stirring at 18° C. and 160 rpm for 24 hours with the mechanical stirrer.

At that time point, the resultant BHA-PA-5MG polyamic acid polymerization solution was sampled and measured for its molecular weight. As a result of a measurement by GPC, its number average molecular weight (Mn) was 34,192, its weight average molecular weight (Mw) was 35,542, and Mw/Mn was 1.039.

In a similar manner as in Example 1, polyimide films were next formed, and their thicknesses, imidation rates and light transmittances were measured. The results are shown in the following table. In the case of the polyimide film 3, however, the final baking was conducted at 160° C.

TABLE 3

| Polyimide film | Doctor blade (μm) | Baking temp. (° C.) | Film thickness (μm) | Imidation rate (%) | Light transmittance (%) | |
|---|---|---|---|---|---|---|
| | | | | | 350 (nm) | 400 (nm) |
| 1 | 25 | 230 | 0.89 | 100 | 90 | 93 |
| 2 | 200 | 230 | 8.73 | 100 | — | 38 |
| 3 | 200 | 160 | 10.0 | 94 | 52 | 72 |

<Measurement of Light Transmittance>

Figure 4:
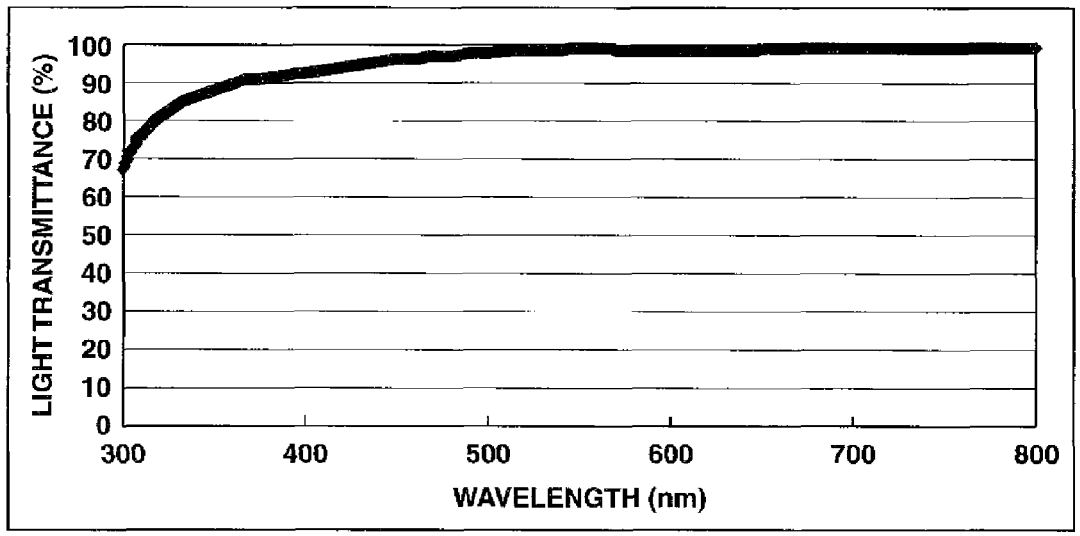
FIG. 4 is a UV-Vis spectrum of a BHA-PA-5MG polyimide of 0.89 μm in film thickness.

As a result of measurements of UV-Vis spectra, the polyimide film 1 had a light transmittance of 90% at 350 nm, and a light transmittance of 93% at 400 nm (see FIG. 4).

Further, thermal characteristics of the polyimide film 2 were as follows:

5% weight loss temperature ($T_5$): 321.9° C.

10% weight loss temperature ($T_{10}$): 351.3° C.

Further, the BHA-PA-5MG polyamic acid polymerization solution was coated onto an 8 cm×10 cm glass plate by using a pipette. Subsequently, the coating was prebaked at 100° C. for 1 hour by using a hot plate, and the glass plate with the prebaked coating carried thereon was then transferred into a drier, in which baking was conducted at 230° C. for 1 hour to form a polyimide film. When the film on the glass plate was dipped in warm water and was then left over at room temperature, the film separated. The film had a thickness of 28 μm and an imidation rate of 99%, and was tough and flexible.

Example 4

Synthesis of BHA-DA-4P Polyamic Acid and Polyimide

[Chemical Formula 14]

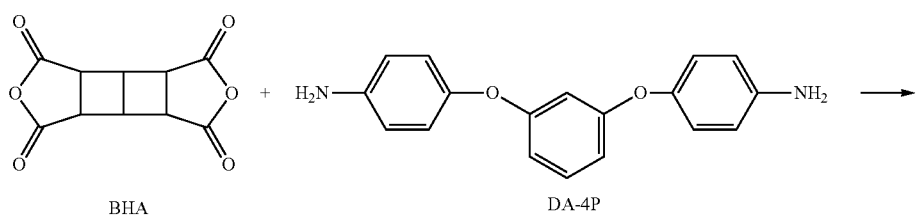

BHA    DA-4P

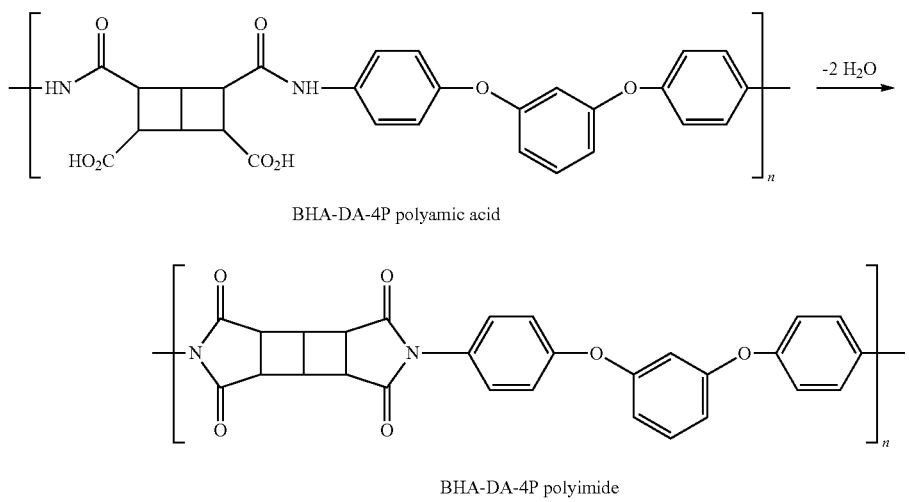

BHA-DA-4P polyamic acid

BHA-DA-4P polyimide 1,3-Bis(4,4'-aminophenoxy)benzene (DA-4P) (0.559 g, 2.00 mmol) and NMP (5.67 g, solid content: 15 wt %) were charged into a dried 4-necked reaction flask, and were then formed into a solution at 18° C. (room temperature) while stirring them with a mechanical stirrer. Subsequently, BHA (0.444 g, 2.00 mmol) was added, followed by stirring at 18° C. and 160 rpm for 48 hours with the mechanical stirrer.

At that time point, the resultant BHA-DA-4P polyamic acid polymerization solution was sampled and measured for its molecular weight. As a result of a measurement by GPC, its number average molecular weight (Mn) was 9,390, its weight average molecular weight (Mw) was 9,462, and Mw/Mn was 1.008.

Next, in a similar manner as in Example 1 except that final baking was conducted at 160° C., polyimide films were formed, and their thicknesses, imidation rates and light transmittances were measured. The results are shown in the following table.

TABLE 4

| Polyimide film | Doctor blade (μm) | Film thickness (μm) | Imidation rate (%) | Light transmittance (%) | |
|---|---|---|---|---|---|
| | | | | 350 (nm) | 400 (nm) |
| 1 | 25 | 1.48 | 68 | 95 | 98 |
| 2 | 200 | 16.9 | 64 | 60 | 83 |

<Measurement of Light Transmittance>

Figure 5:
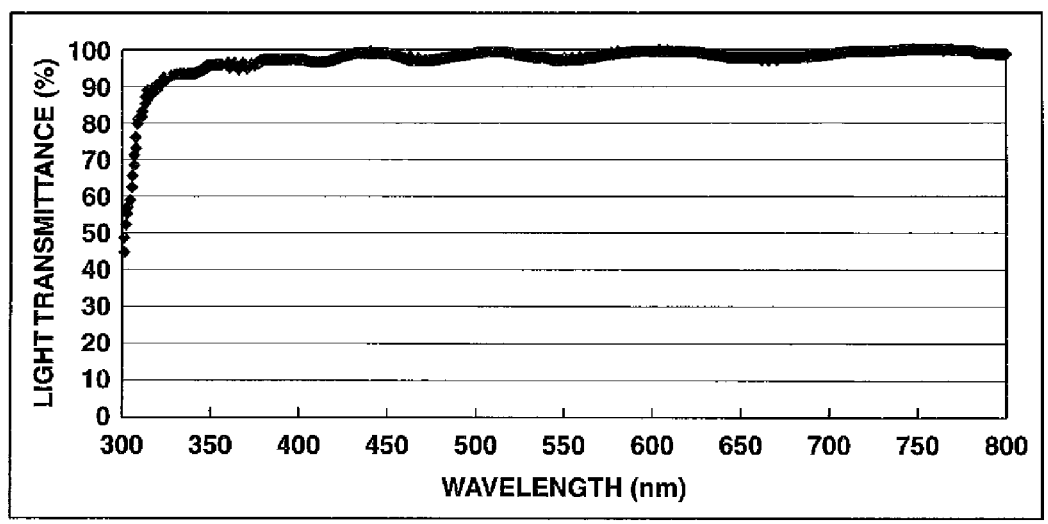
FIG. 5 is a UV-Vis spectrum of a BHA-DA-4P polyimide of 1.48 μm in film thickness.

As a result of measurements of UV-Vis spectra, the polyimide film 1 had a light transmittance of 95% at 350 nm, and a light transmittance of 98% at 400 nm (see FIG. 5).

Figure 6:
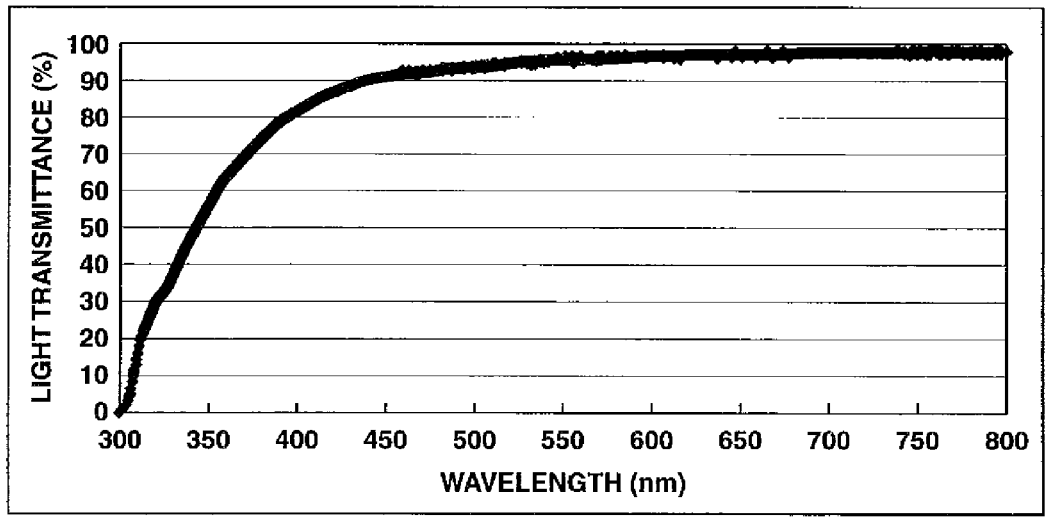
FIG. 6 is a UV-Vis spectrum of a BHA-DA-4P polyimide of 16.9 μm in film thickness.

The polyimide film 2 had a light transmittance of 60% at 350 nm, and a light transmittance of 83% at 400 nm (see FIG. 6).

Further, the BHA-DA-4P polyamic acid polymerization solution was coated onto an 8 cm×10 cm glass plate by using a pipette. Subsequently, the coating was prebaked at 100° C. for 1 hour by using a hot plate, and the glass plate with the prebaked coating carried thereon was then transferred into a drier, in which baking was conducted at 160° C. for 3 hours to form a polyimide film. When the film on the glass plate was dipped in warm water and was then left over at room temperature, the film separated. The film had a thickness of 62 μm and an imidation rate of 81%, and was tough and flexible.

The results of tensile tests of the film were as follows:

(1) Specimen:
Thickness (mm)=0.062
Width (mm)=4.0
Gage length (mm)=10
Cross-sectional area (mm$^2$)=0.248
Load-bearing capacity (kgf/mm$^2$)=5.99 (58.7 MPa)
Rupturable load (kgf)=0.798
Elongation at rupture (mm) 1.990
Elongation at rupture (%)=19.90
Rupture stress (kgf/mm$^2$)=3.22 (31.6 MPa)
Maximum load (kgf)=3.884
Maximum stress (kgf/mm$^2$)=15.66 (153.6 MPa)
Young's modulus (kgf/mm$^2$)=31.54 (0.309 GPa)

(2) Specimen:
Thickness (mm)=0.060
Width (mm)=6.0
Gage length (mm)=10
Cross-sectional area (mm$^2$)=0.360
Rupturable load (kgf)=4.893
Elongation at rupture (mm)=1.201
Elongation at rupture (%)=12.01
Rupture stress (kgf/mm$^2$)=13.59 (133.3 MPa)
Maximum load (kgf)=5.000
Maximum stress (kgf/mm$^2$)=13.89 (136.2 MPa)
Young's modulus (kgf/mm$^2$)=24.02 (0.236 GPa)

From the foregoing, high rupture stress and elongation rate were shown.

Example 5

Synthesis of BHA-MBCA Polyamic Acid and Polyimide

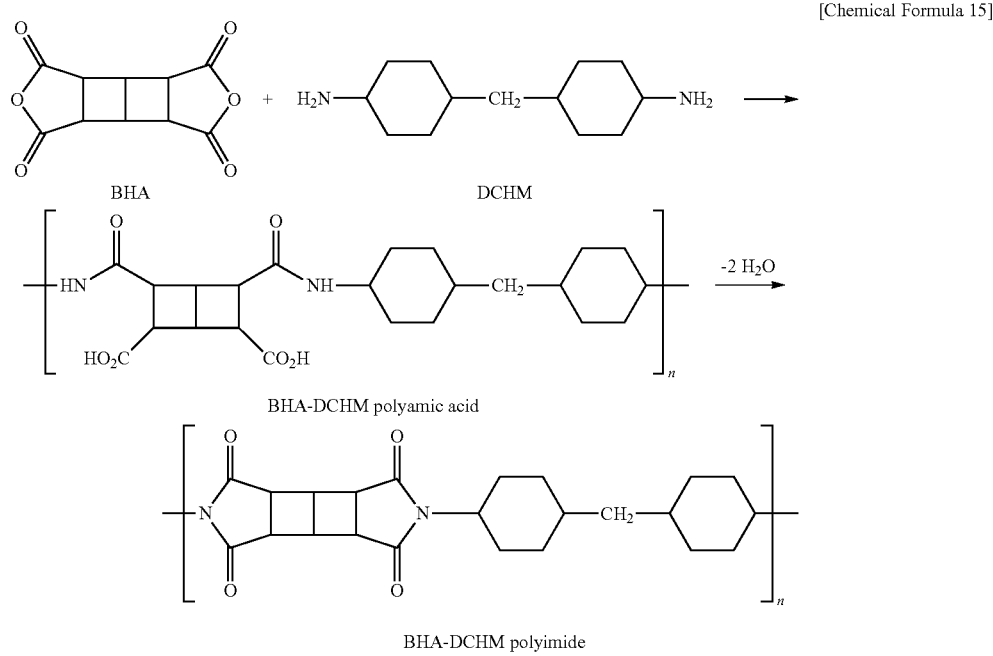

[Chemical Formula 15]

4,4'-Diaminodicyclohexylmethane (DCHM) (0.421 g, 2.00 mmol) and cresol (4.90 g, solid content: 15 wt %) were charged into a dried 4-necked reaction flask, and were then formed into a solution at 18° C. (room temperature) while stirring them with a mechanical stirrer. Subsequently, BHA (0.444 g, 2.00 mmol) was added, followed by stirring at 18° C. and 160 rpm for 24 hours with the mechanical stirrer.

Further, the thus-obtained BHA-MBCA polyamic acid polymerization solution was coated onto an 8 cm×10 cm glass plate by using a pipette. Subsequently, the coating was prebaked at 100° C. for 1 hour by using a hot plate, and the glass plate with the prebaked coating carried thereon was then transferred into a drier, in which baking was conducted at 230° C. for 1 hour to form a polyimide film. When the film on the glass plate was dipped in warm water and was then left over at room temperature, the film separated. The film had a thickness of 50 μm and an imidation rate of 99%, and was tough and flexible. Its 10% weight loss temperature ($T_{10}$) was 285° C.

The results of a tensile test of the film were as follows:
(3) Specimen:
  Thickness (mm)=0.050
  Width (mm)=5.0
  Gage length (mm)=10
  Cross-sectional area (mm$^2$)=0.250
  Load-bearing capacity (kgf/mm$^2$)=13.32 (130.6 MPa)
  Rupturable load (kgf)=4.348
  Elongation at rupture (mm)=1.390
  Elongation at rupture (%)=13.90
  Rupture stress (kgf/mm$^2$)=17.39 (170.5 MPa)
  Maximum load (kgf)=4.869
  Maximum stress (kgf/mm$^2$) 19.48 (191.0 MPa)
  Young's modulus (kgf/mm$^2$)=237.33 (2.327 GPa)

From the foregoing, high rupture stress and elongation rate were shown.

Next, in a similar manner as in Example 1 except that the final baking temperature for the resultant BHA-MBCA polyamic acid polymerization solution was changed from 230° C. to 160° C., polyimide films were formed, and their thicknesses, imidation rates and light transmittances were measured. The results are shown in the following table.

TABLE 5

| Polyimide film | Doctor blade (μm) | Film thickness (μm) | Imidation rate (%) | Light transmittance (%) 350 (nm) | Light transmittance (%) 400 (nm) |
|---|---|---|---|---|---|
| 1 | 25 | 1.28 | 58 | 95 | 98 |
| 2 | 200 | 21.4 | 59 | 75 | 78 |

<Measurement of Light Transmittance>

Figure 7:
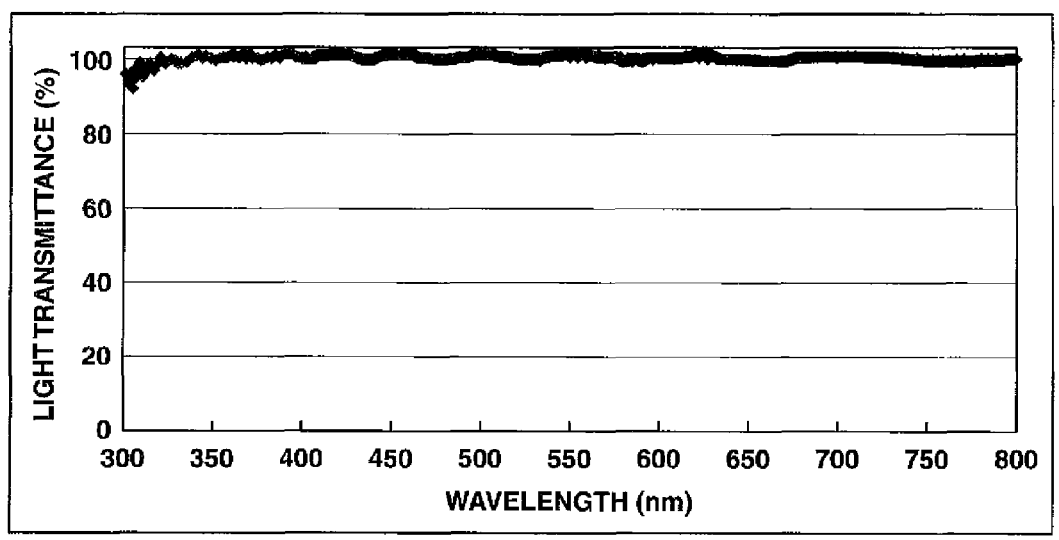
FIG. 7 is a UV-Vis spectrum of a BHA-MBCA polyimide of 1.28 μm in film thickness.

As a result of measurement of UV-Vis spectra, the polyimide film 1 had a light transmittance of 95% at 350 nm, and a light transmittance of 98% at 400 nm (see FIG. 7).

Figure 8:
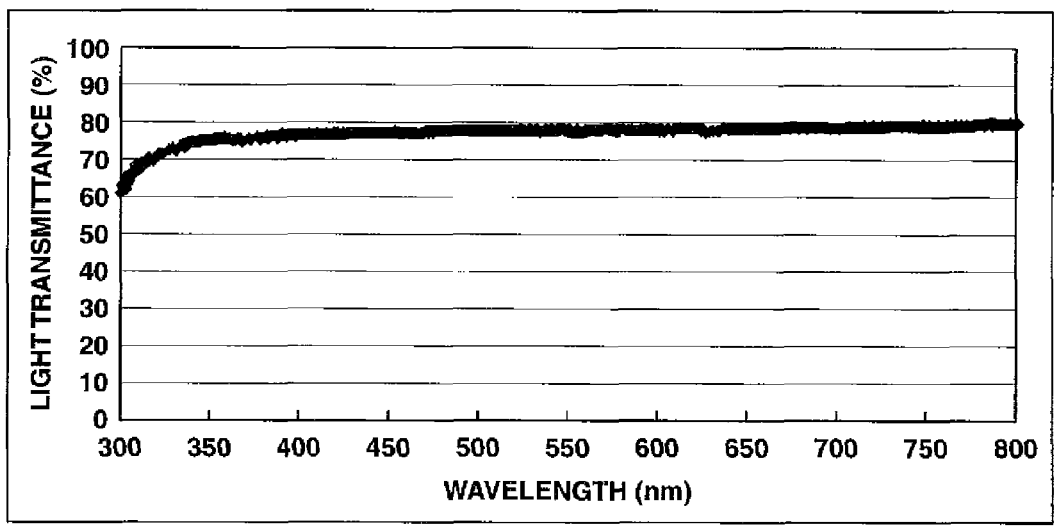
FIG. 8 is a UV-Vis spectrum of a BHA-MBCA polyimide of 21.4 μm in film thickness.

The polyimide film 2 had a light transmittance of 75% at 350 nm, and a light transmittance of 78% at 400 nm (see FIG. 8).

Example 6

Synthesis of BHA-BBH Polyamic Acid and Polyimide

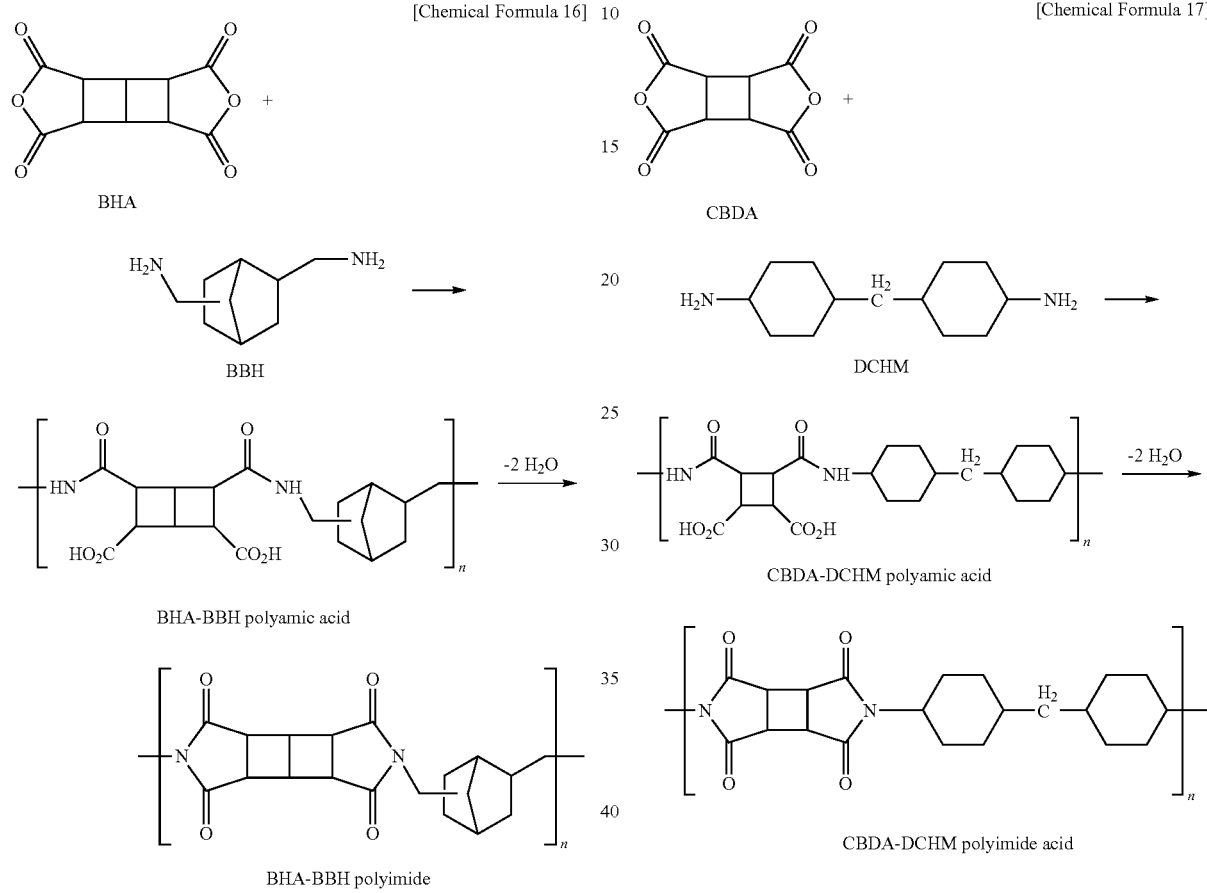

2,5(6)-Bis(aminomethyl)bicyclo[2.2.1]heptane (BBH) (0.309 g, 2.00 mmol) and cresol (4.27 g, solid content: 15 wt %) were charged into a dried 4-necked reaction flask, and were then formed into a solution at 18° C. (room temperature) while stirring them with a mechanical stirrer. Subsequently, BHA (0.444 g, 2.00 mmol) was added, followed by stirring at 18° C. and 160 rpm for 72 hours with the mechanical stirrer.

Further, the thus-obtained BHA-BBH polyamic acid polymerization solution was coated onto an 8 cm×10 cm glass plate by using a pipette. Subsequently, the coating was prebaked at 100° C. for 1 hour by using a hot plate, and the glass plate with the prebaked coating carried thereon was then transferred into a drier, in which baking was conducted at 160° C. for 1 hour to form a polyimide film.

The film had a thickness of 32 μm and an imidation rate of 98%.

Further, as a result of a measurement of its light transmittance, the light transmittance was 46% at 450 nm.

Comparative Example 1

Synthesis of CBDA-DCHM Polyamic Acid and Polyimide 4,4'-Diaminodicyclohexylmethane (DCHM) (1.05 g, 5.00 mmol) and cresol (11.5 g, solid content: 15 wt %) were charged into a dried 4-necked reaction flask, and were then formed into a solution at 18° C. (room temperature) while stirring them with a mechanical stirrer. Subsequently, 1,2,3,4-cyclobutanetetracarboxylic-1,2:3,4-dianhydride (CBDA) (0.980 g, 5.00 mmol) was added, followed by stirring at 45° C. and 160 rpm for 1 hour with the mechanical stirrer. Stirring was then conducted at 20° C. and 160 rpm for 23 hours.

The thus-obtained CBDA-DCHM polyamic acid polymerization solution was next coated dropwise onto an 8 cm×10 cm glass plate by using a pipette. Subsequently, the coating was prebaked at 100° C. for 30 minutes on a hot plate, and the glass plate with the prebaked coating carried thereon was then placed in a drier controlled at 160° C., in which baking was conducted for 1 hour to form a polyimide film. The resulting film had transparency but was cracked in pieces, so that it was unable to peel it off as a single piece of film. As a result of a measurement of the thickness of one of cracked pieces, it was 14.5 μm thick.

Comparative Example 2

Synthesis of CBDA-DA-4P Polyamic Acid and Polyimide

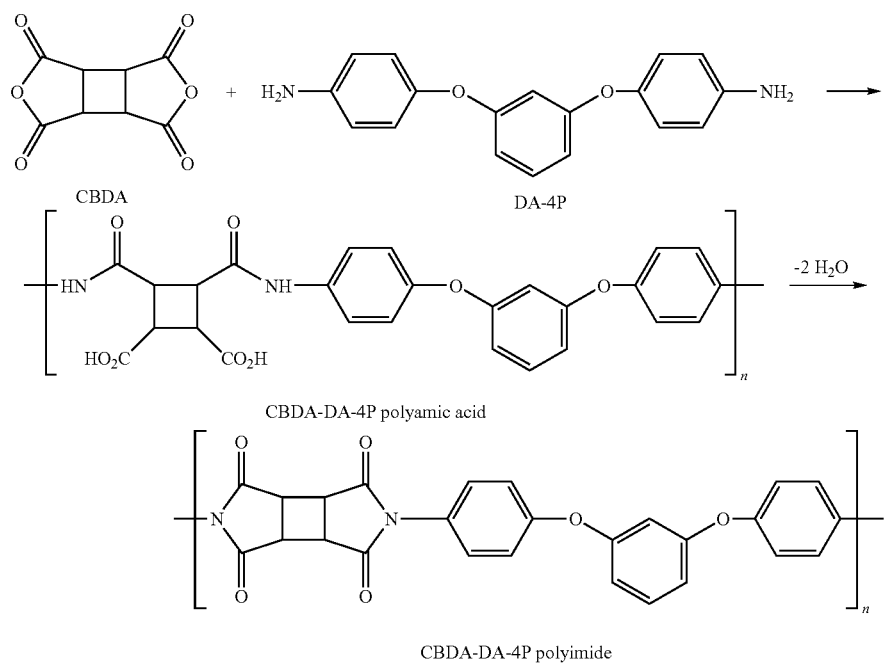

[Chemical Formula 18]

CBDA-DA-4P polyamic acid

CBDA-DA-4P polyimide 1,3-Bis(4,4'-aminophenoxy)benzene (DA-4P) (0.559 g, 2.00 mmol) and NMP (5.39 g, solid content: 15 wt %) were charged into a dried 4-necked reaction flask, and were then formed into a solution at 18° C. (room temperature) while stirring them with a mechanical stirrer. Subsequently, 1,2,3,4-cyclobutanetetracarboxylic-1,2:3,4-dianhydride (CBDA) (0.392 g, 2.00 mmol) was added, followed by stirring at 18° C. and 160 rpm for 24 hours with the mechanical stirrer.

The thus-obtained CBDA-DA-4P polyamic acid polymerization solution was next coated dropwise onto an 8 cm×10 cm glass plate by using a pipette. Subsequently, the coating was prebaked at 100° C. for 2 hours on a hot plate, and the glass plate with the prebaked coating carried thereon was then placed in a drier controlled at 160° C., in which baking was conducted for 2 hours to form a polyimide film. The resulting film had a pale brown color, and was separated from the glass plate. When the film was picked by tweezers, the film was broken into pieces so that it was unable to take it out as a single piece of film.

The invention claims is:

1. A polyamic acid comprising
at least 10 mol % of repeating units represented by the formula [1] or formula [2],

[Chemical Formula 1]

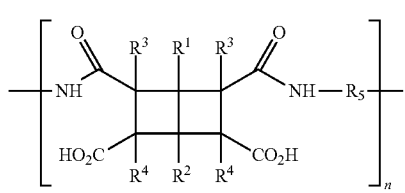

[1]

-continued

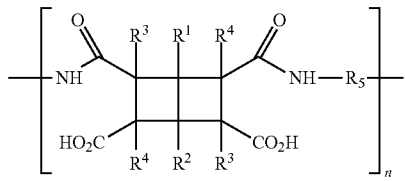

[2]

wherein $R^1$ and $R^2$ each independently represent a hydrogen atom or an alkyl group having 1 to 10 carbon atoms; $R^3$ and $R^4$ each independently represent a hydrogen atom, a halogen atom, an alkyl group having 1 to 10 carbon atoms, a phenyl group, or $R^3$ and $R^4$ on adjacent carbon atoms are fused together to represent a cycloalkyl group having 3 to 8 carbon atoms or to represent a phenyl group; $R^5$ represents a divalent organic group; and n stands for an integer of at least 2.

2. A polyimide comprising
at least 10 mol % of repeating units represented by the formula [3] or formula [4],

[Chemical Formula 2]

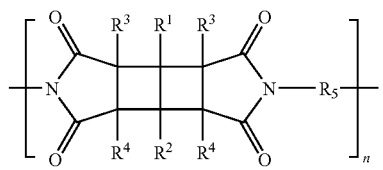

[3]

-continued

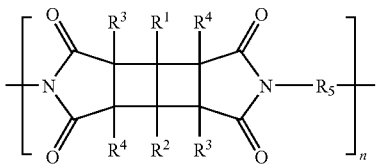

wherein $R^1$ and $R^2$ each independently represent a hydrogen atom or an alkyl group having 1 to 10 carbon atoms; $R^3$ and $R^4$ each independently represent a hydrogen atom, a halogen atom, an alkyl group having 1 to 10 carbon atoms, a phenyl group, or $R^3$ and $R^4$ on adjacent carbon atoms are fused together to represent a cycloalkyl group having 3 to 8 carbon atoms or to represent a phenyl group; $R^5$ represents a divalent organic group; and n stands for an integer of at least 2.

3. The polyamic acid according to claim 1, which has a number average molecular weight of 5,000 to 300,000.

4. The polyamic acid according to claim 1, wherein $R^1$, $R^2$, $R^3$ and $R^4$ are a hydrogen atom.

5. The polyamic acid according to claim 1, wherein $R^1$ and $R^2$ are a hydrogen atom, and at least one of $R^3$ and $R^4$ is a methyl group.

6. The polyimide according to claim 2, wherein $R^1$, $R^2$, $R^3$ and $R^4$ are a hydrogen atom.

7. The polyimide according to claim 2, wherein $R^1$ and $R^2$ are a hydrogen atom, and at least one of $R^3$ and $R^4$ is a methyl group.

8. The polyamic acid according to claim 1, wherein in the formula [1] and formula [2], $R^5$ is a divalent organic group derived from an alicyclic diamine or aliphatic diamine.

9. The polyimide according to claim 2, wherein in the formula [3] and formula [4], $R^5$ is a divalent organic group derived from an alicyclic diamine or aliphatic diamine.

10. A film comprising a polyimide according to any one of claims 2, 6, 7 and 9.

* * * * *